(12) United States Patent
Sato et al.

(10) Patent No.: US 11,449,990 B2
(45) Date of Patent: Sep. 20, 2022

(54) MEDICAL IMAGE PROCESSING APPARATUS AND MEDICAL IMAGE PROCESSING SYSTEM

(71) Applicant: Canon Medical Systems Corporation, Otawara (JP)

(72) Inventors: Shin Sato, Tokyo (JP); Tomoko Miyata, Tokyo (JP); Hiromasa Yamagishi, Otawara (JP); Taisuke Iwamura, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 339 days.

(21) Appl. No.: 16/840,558

(22) Filed: Apr. 6, 2020

(65) Prior Publication Data

US 2020/0327666 A1  Oct. 15, 2020

(30) Foreign Application Priority Data

Apr. 10, 2019  (JP) .............................. JP2019-075061

(51) Int. Cl.
*G06T 7/70* (2017.01)
*G16H 30/40* (2018.01)
*G06T 7/00* (2017.01)
*G06T 7/60* (2017.01)
*G06T 7/11* (2017.01)
(Continued)

(52) U.S. Cl.
CPC ............ *G06T 7/0012* (2013.01); *A61B 5/055* (2013.01); *G06T 3/60* (2013.01); *G06T 7/11* (2017.01); *G06T 7/60* (2013.01); *G06T 7/70* (2017.01); *G16H 30/40* (2018.01); *A61B 2576/00* (2013.01); *G06T 2207/10088* (2013.01); *G06T 2207/20092* (2013.01); *G06T 2207/20224* (2013.01); *G06T 2207/30096* (2013.01); *G06T 2207/30101* (2013.01)

(58) Field of Classification Search
CPC .......... G06T 7/0012; G06T 7/30; G06T 7/70; G06T 7/73; G06T 2207/30016; G06T 2207/30096; G06T 2207/30101; G16H 30/40; A61B 5/0042; A61B 5/02014; A61B 5/055
See application file for complete search history.

(56) References Cited

U.S. PATENT DOCUMENTS

| 10,552,672 B2 | 2/2020 | Iwase et al. ........ G06K 9/00362 |
| 2006/0074711 A1 | 4/2006 | Mahesh et al. ................... 705/2 |

(Continued)

FOREIGN PATENT DOCUMENTS

| JP | 2008-515119 A | 5/2008 |
| JP | 2009-157527 A | 7/2009 |

(Continued)

*Primary Examiner* — Andrew W Johns
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry acquires coordinate information of at least one detection position of a cerebrovascular lesion for three-dimensional MR image data relating to a head part, and generates a two-dimensional display image which visualize a part of or all of the at least one detection position based on the three-dimensional MR image data and the coordinate information.

20 Claims, 12 Drawing Sheets

(51) Int. Cl.
  *G06T 3/60* (2006.01)
  *A61B 5/055* (2006.01)

(56) References Cited

U.S. PATENT DOCUMENTS

2020/0020435 A1* 1/2020 Annavi ................. G16H 30/40
2020/0116808 A1* 4/2020 Taher et al. .......... A61B 5/4064
2022/0114723 A1* 4/2022 Kim et al. ............ G06T 11/006

FOREIGN PATENT DOCUMENTS

JP   2011-139821 A   7/2011
JP   2017-055781 A   3/2017

* cited by examiner

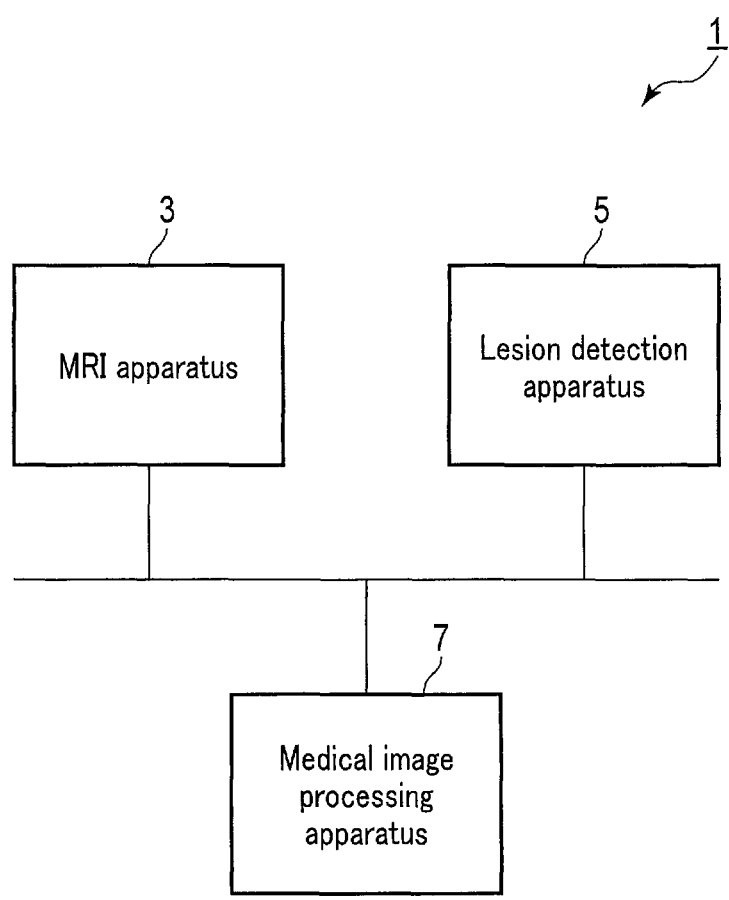
F I G. 1

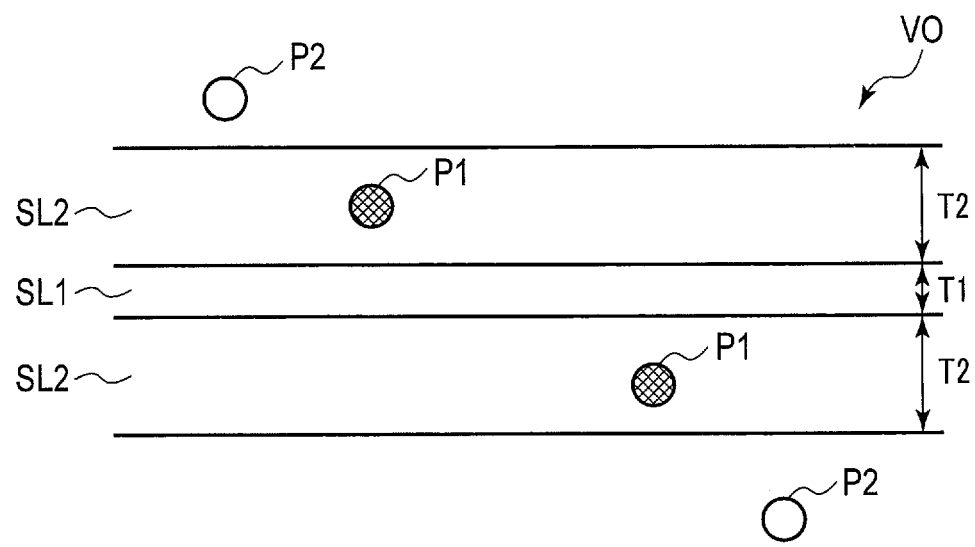
F I G. 8
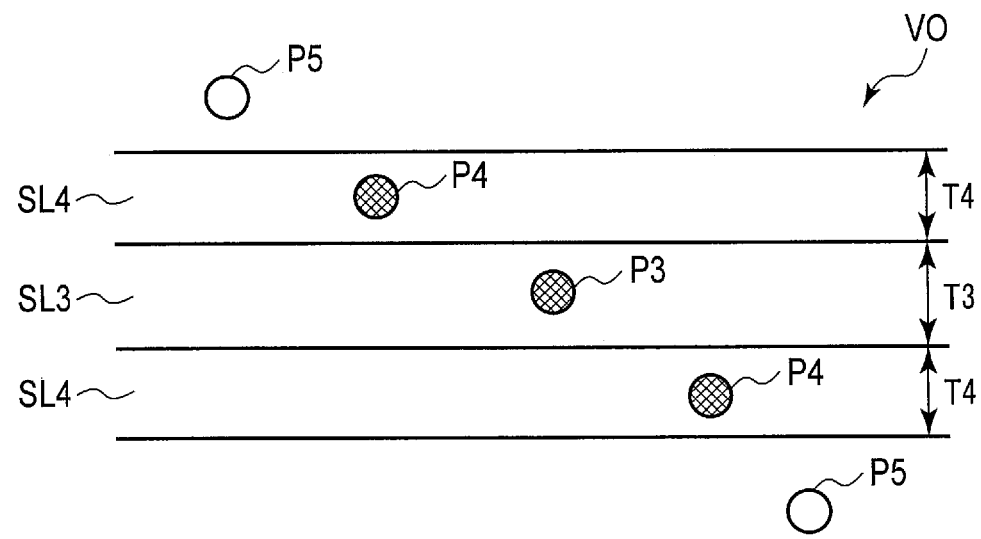
F I G. 9

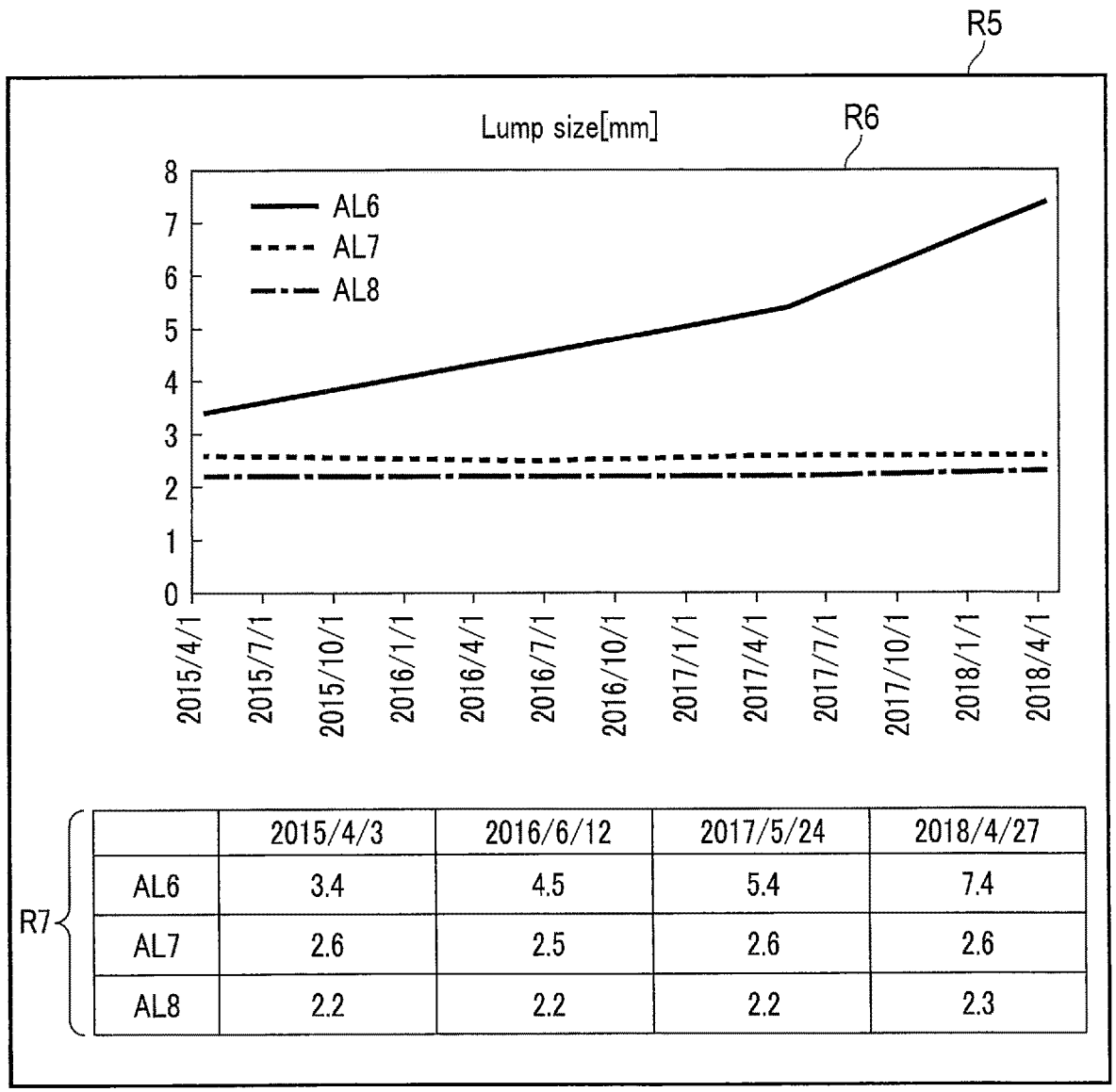
F I G. 12

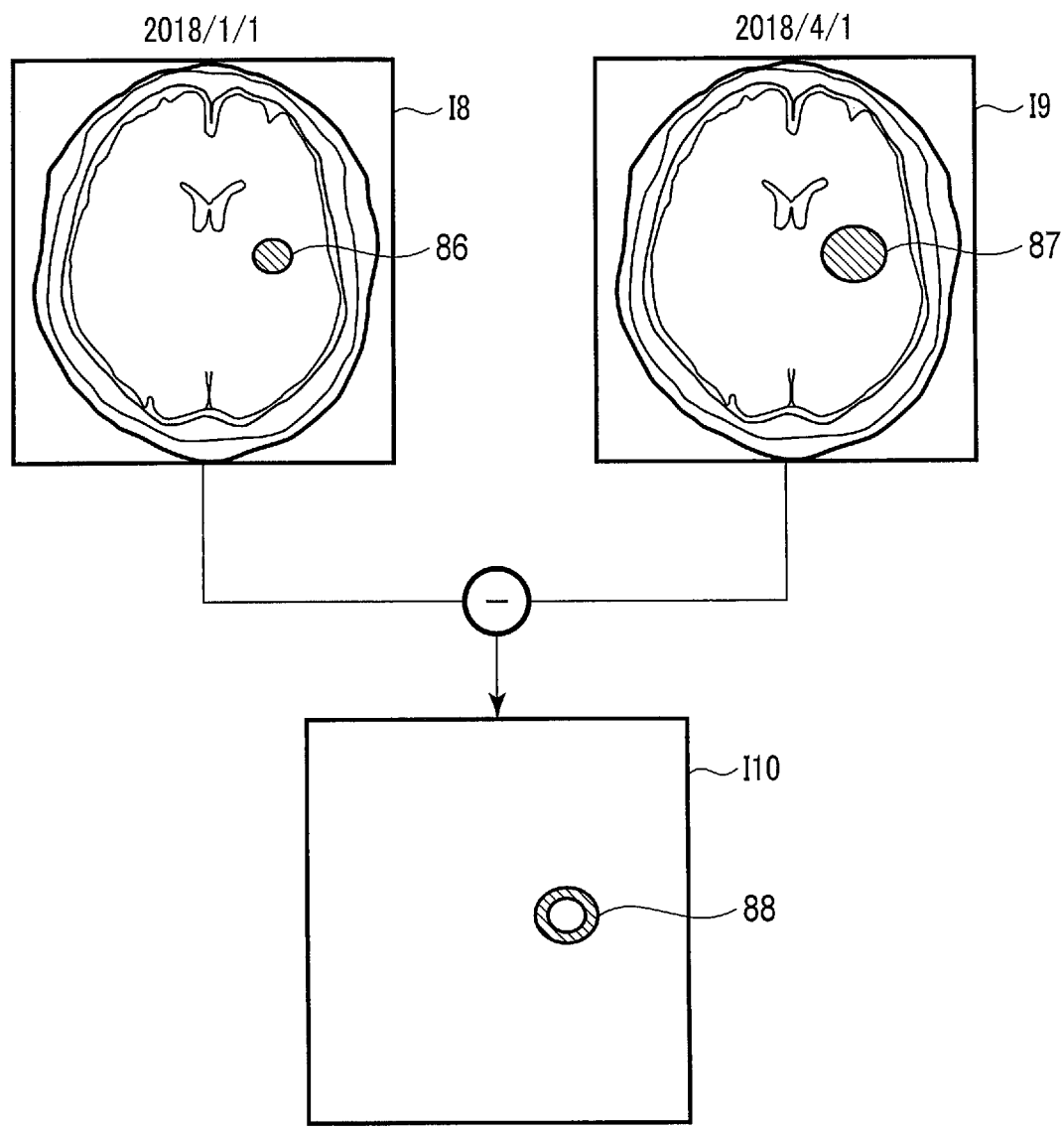
F I G. 13

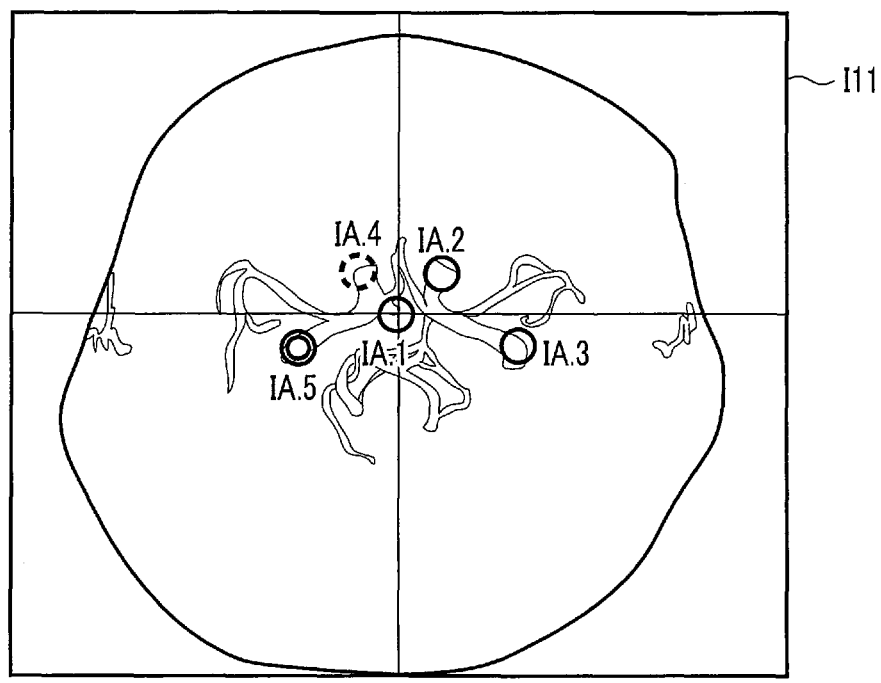
F I G. 14

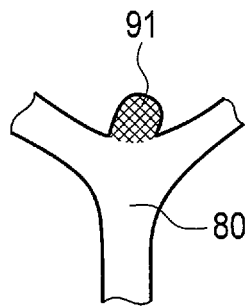
F I G. 15
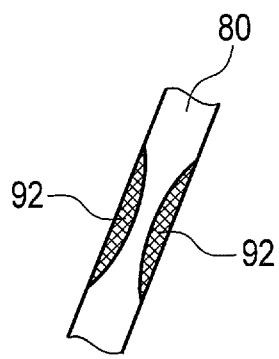
F I G. 16
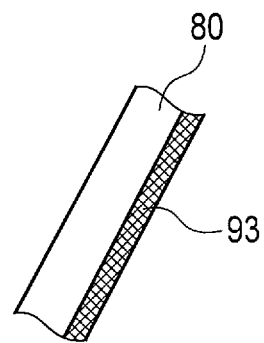
F I G. 17

MEDICAL IMAGE PROCESSING APPARATUS AND MEDICAL IMAGE PROCESSING SYSTEM

CROSS-REFERENCE TO RELATED APPLICATIONS

This application is based upon and claims the benefit of priority from the Japanese Patent Application No. 2019-075061, filed Apr. 10, 2019 the entire contents of which are incorporated herein by reference.

FIELD

Embodiments described herein relate generally to a medical image processing apparatus and a medical image processing system.

BACKGROUND

There exists a technique to detect a cerebral aneurysm that is visualized on a medical image by utilizing artificial intelligence (AI). A picture archiving and communication system (PACS) computer receives a detection result obtained by the AI in a form defined by a grayscale softcopy presentation state (GSPS) in a Digital Imaging and Communication in Medicine (DICOM) standard. With the GSPS, a circular mark, etc. is painted on a detection position in a cross-sectional image to indicate the detection position.

Since a user does not know where the detection position of the cerebral aneurysm is, the user must visually confirm all of the cross-sectional images one by one. This is not only time-consuming, but may also result in oversight by the user.

BRIEF DESCRIPTION OF THE DRAWINGS

FIG. 1 shows a configuration of a medical image processing system.

FIG. 8 is a schematic view showing an annotation corresponding to a proximal detection position displayed on an MPR image.

FIG. 9 is a schematic view showing an annotation corresponding to a proximal detection position displayed on a slab image.

FIG. 12 shows an example of a lump size report.

FIG. 13 is a schematic view showing a generation process of an image temporal difference.

FIG. 14 shows a display example of detection positions of an unruptured cerebral aneurysm, an intracranial artery stenosis, and a cerebrovascular dissection.

FIG. 15 shows a highlighted example of an unruptured cerebral aneurysm.

FIG. 16 shows a highlighted example of an intracranial artery stenosis.

FIG. 17 shows a highlighted example of a cerebrovascular dissection.

DETAILED DESCRIPTION

Figure 2:
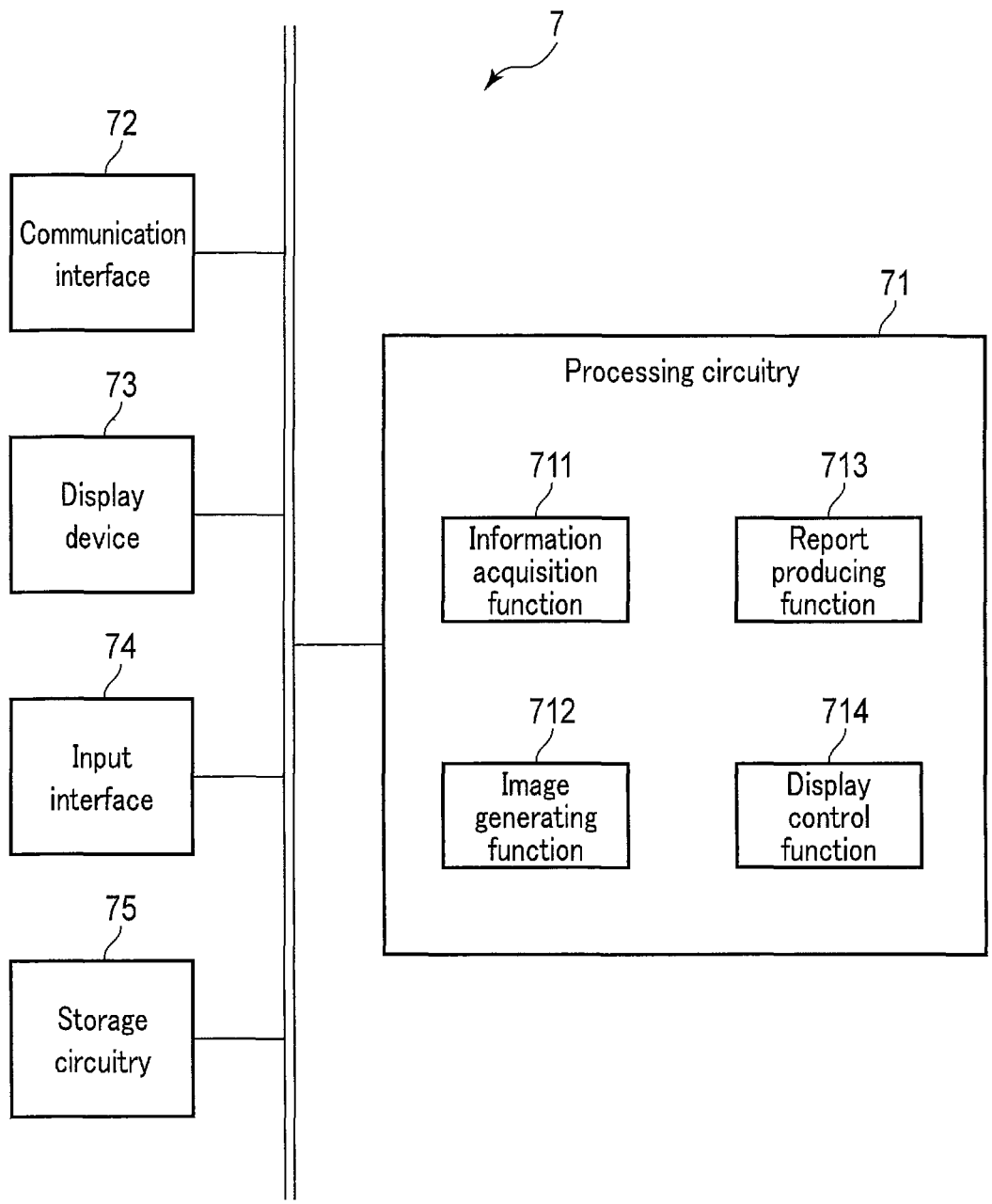
FIG. 2 shows a configuration of a medical image processing apparatus of FIG. 1.

In general, according to one embodiment, a medical image processing apparatus comprises processing circuitry. The processing circuitry acquires coordinate information of at least one detection position of a cerebrovascular lesion for three-dimensional MR image data relating to a head part, and generates a two-dimensional display image which visualize a part of or all of the at least one detection position based on the three-dimensional MR image data and the coordinate information.

Hereinafter, the medical image processing apparatus and the medical image processing system according to the present embodiment will be explained with reference to the drawings.

FIG. 1 shows a configuration of a medical image processing system 1. As shown in FIG. 1, the medical image processing system 1 has a magnetic resonance imaging apparatus (MRI apparatus) 3, a lesion detection apparatus 5, and a medical image processing apparatus 7 which are connected to each other via a network.

The MRI apparatus 3, for example, applies an RF pulse from an RF coil, excites a target atomic nucleus inside a subject placed in a static magnetic field, and acquires an MR signal that is generated from the target atomic nucleus by the RF coil. The MRI apparatus 3 then generates MR image data that represents spatial distribution of the target atomic nucleus based on the MR signal from the RF coil. The MRI apparatus 3 in the present embodiment performs MR imaging on a three-dimensional region set in an examination portion of the subject, and generates three-dimensional MR image data relating to the examination portion. The three-dimensional MR image data may be multi-slice image data defined by a group of a plurality of two-dimensional slice images arranged in a line, or may be volume data defined by a group of a plurality of voxels arranged three-dimensionally. The examination portion of the subject according to the present embodiment is assumed to be a head part. The two-dimensional slice image is synonymous with an axial image.

The lesion detection apparatus 5 applies detection processing of a cerebrovascular lesion on the three-dimensional MR image data and outputs a detection result. By the detection processing, all of the image regions suspected of a cerebrovascular lesion included in the three-dimensional MR image data are detected. The detection result includes coordinate information, painting information, and additional information for each detection position of the cerebrovascular lesion. The detection position according to the present embodiment is synonymous with the image region detected as the cerebrovascular lesion. The coordinate information is character information relating to a coordinate of the detection position in an image space defining the three-dimensional MR image data. For example, the coordinate information is defined as (x-axis coordinate, y-axis coordinate, slice number) in a case where the three-dimensional MR image data is multi-slice image data, and is defined as (x-axis coordinate, y-axis coordinate, z-axis coordinate) in a case where the three-dimensional MR image data is volume data. The painting information is information relating to painting a mark to be added to the three-dimensional MR image data. The mark is also referred to as an annotation.

Specifically, the painting information includes the shape of the annotation and coordinate information for painting the annotation. The additional information is character information of the size, score, and location (portion), etc. of the detected cerebrovascular lesion. The additional information may be defined in accordance with a data format of the DICOM standard, or may be defined in accordance with a data format of a non-DICOM standard, such as a Java Script Object Notation (JSON) or an Extensible Markup Language (XML). The lesion detection apparatus 5 is a computer comprising a central processing unit (CPU), a memory, a display, an input interface, and a communication interface as a hardware configuration.

The medical image processing apparatus 7 displays the three-dimensional MR image data acquired by the MRI apparatus 3, and the detection result relating to the cerebrovascular lesion detected by the lesion detection apparatus 5. The medical image processing apparatus 7 is a computer configuring the PACS.

FIG. 2 shows a configuration of the medical image processing apparatus 7 of FIG. 1. As shown in FIG. 2, the medical image processing apparatus 7 includes processing circuitry 71, a communication interface 72, a display device 73, an input interface 74, and storage circuitry 75.

The processing circuitry 71 includes processors such as a CPU and a graphics processing unit (GPU). By activating a program installed in the storage circuitry 75, etc., the processor realizes an information acquisition function 711, an image generating function 712, a report producing function 713, and a display control function 714, etc. Each of the functions 711 to 714 is not limited to the case of being realized by a single processing circuitry. The processing circuitry may be configured by combining a plurality of independent processors, and may realize each of the functions 711 to 714 by having each of the processors execute the program.

By the information acquisition function 711, the processing circuitry 71 acquires the three-dimensional MR image data from the MRI apparatus 3 via the communication interface 72, and acquires the detection result of the cerebrovascular lesion from the lesion detection apparatus 5. In the case where the three-dimensional MR image data and/or the detection result is stored in the storage circuitry 75, the processing circuitry 71 acquires the three-dimensional MR image data and/or the detection result from the storage circuitry 75. Other than the three-dimensional MR image data and the detection result, the processing circuitry 71 is able to acquire various information.

By the image generating function 712, the processing circuitry 71 generates two-dimensional display image data by applying three-dimensional image processing to the three-dimensional MR image data. As the three-dimensional image processing, it is also possible to perform image processing including multi-planar reconstruction (MPR) processing, volume rendering and surface rendering, pixel value projection processing, and curved MPR (CPR) processing, etc. As the pixel value projection processing, any projection processing such as maximum value projection processing, minimum value projection processing, and average value projection processing is applicable. Based on the three-dimensional MR image data and the coordinate information of the detection position included in the detection result, the processing circuitry 71 generates a two-dimensional display image which visualize a part of or all of at least one detection position detected by the lesion detection apparatus 5.

By the report producing function 713, the processing circuitry 71 produces a report relating to the detection result based on the detection result relating to the cerebrovascular lesion.

By the display control function 714, the processing circuitry 71 displays various information on the display device 73. For example, the processing circuitry 71 displays the display image generated by the image generating function 712 on the display device 73. The processing circuitry 71 may also display the report produced by the report producing function 713 on the display device 73.

The communication interface 72 is an interface for performing data communications between the MRI apparatus 3 and the lesion detection apparatus 5 included in the medical image processing system 1. For example, the communication interface 72 receives the three-dimensional MR image data from the MRI apparatus 3, and the detection result from the lesion detection apparatus 5.

The display device 73 displays various information in accordance with the display control function 714 of the processing circuitry 71. For example, the display device 73 displays the display image generated by the image generating function 712. As the display device 73, for example, a liquid crystal display (LCD), a cathode ray tube (CRT) display, an organic electro luminescence display (OELD), a plasma display, or any other displays can be used as appropriate. Furthermore, the display device 73 may be a projector.

The input interface 74 receives various input operations from a user, converts the received input operation into an electric signal, and outputs the signal to the processing circuitry 71. Specifically, the input interface 74 is connected to input devices such as a mouse, a keyboard, a trackball, a switch, a button, a joy stick, a touch pad, and a touch panel display. The input interface 74 outputs to the processing circuitry 71 an electric signal in accordance with the input operation performed on the input device. Furthermore, the input device connected to the input interface 74 may also be an input device provided on other computers that are connected via the network, etc.

The storage circuitry 75 is a storage device, such as a read only memory (ROM) or random access memory (RAM), a hard disk drive (HDD), a solid state drive (SSD), and an integrated circuit storage device that store various information. Other than the above storage device, the storage circuitry 75 may be a portable storage medium, such as a compact disc (CD), a digital versatile disc (DVD), and a flash memory, or a driving device that reads and writes various information between semiconductor memory devices, etc. Furthermore, the storage circuitry 75 may be inside other computers that are connected to the medical image processing apparatus 7 via a network. For example, the storage circuitry 75 stores the three-dimensional MR image data received from the MRI apparatus 3 by the communication interface 72, and the detection result received from the lesion detection apparatus 5. Furthermore, the storage circuitry 75 stores an image display program.

Hereinafter, an operation example of the medical image processing system 1 according to the present embodiment will be explained.

Figure 3:
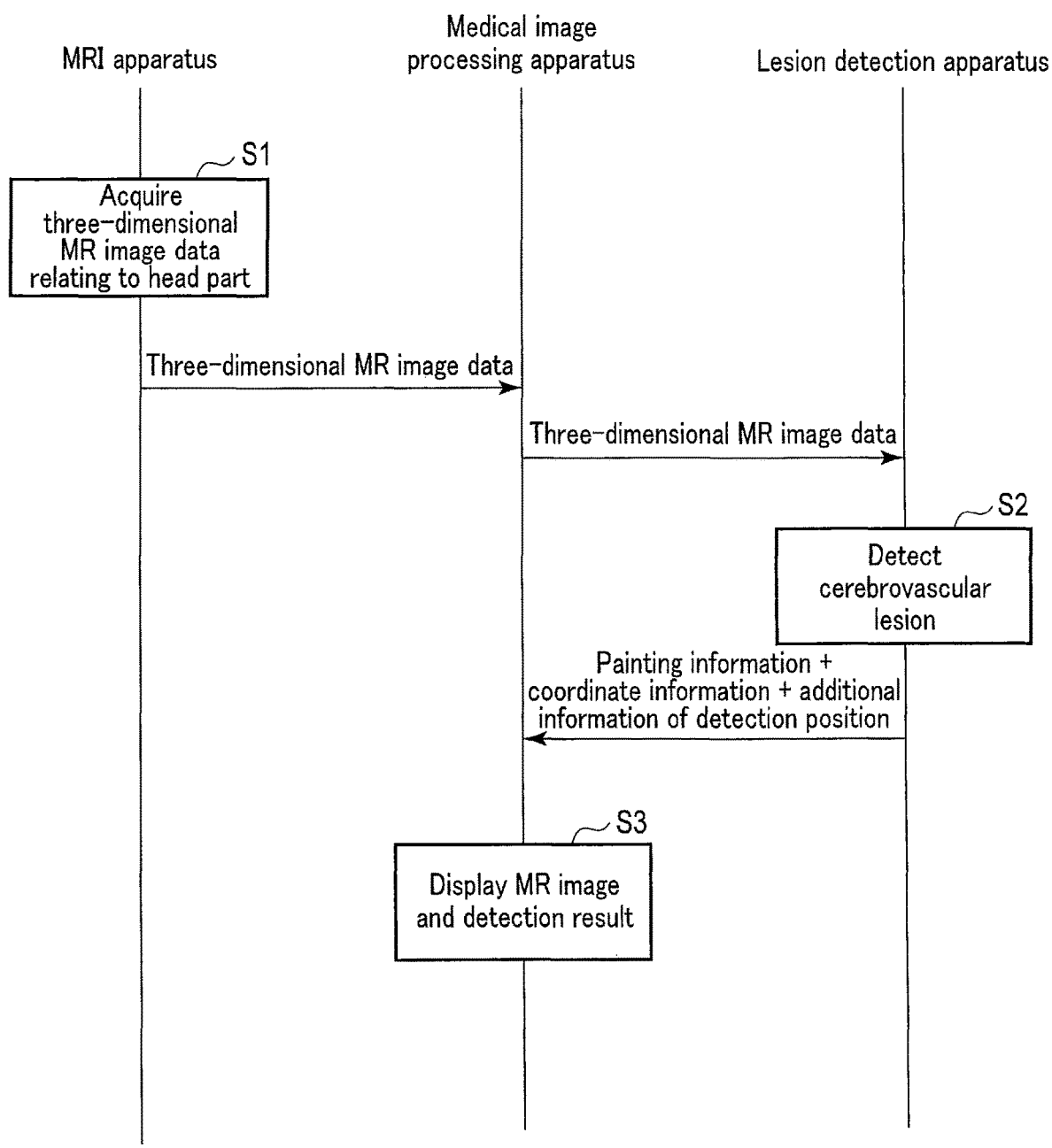
FIG. 3 shows a flow of an operation of the medical image processing system of FIG. 1.

FIG. 3 shows a flow of the operation of the medical image processing system 1. As shown in FIG. 3, the MRI apparatus 3 acquires three-dimensional MR image data relating to a head part of a subject (step S1). As a data acquisition scheme, an MR angiography (MRA) that emphasizes the contrast of a blood vessel of the head part is adopted. The MRA may be a non-contrast MRA or contrast MRA. As the non-contrast MRA, a time-of-flight (TOF) method or a phase contrast (PC) method may be used. The MRI apparatus 3 converts the data format of the acquired three-dimensional MR image data into a DICOM format. The MRI apparatus 3 transmits the three-dimensional MR image data in the DICOM format to the medical image processing apparatus 7.

The communication interface 72 of the medical image processing apparatus 7 receives the three-dimensional MR image data from the MRI apparatus 3. The received three-dimensional MR image data is stored in the storage circuitry 75. The communication interface 72 then transmits the three-dimensional MR image data to the lesion detection apparatus 5. For example, in the case where the three-dimensional MR image data from the MRI apparatus 3 is image data that relates to the head part of the subject, in order to detect the cerebrovascular lesion, the communication interface 72 transmits the three-dimensional MR image data to the lesion detection apparatus 5.

The lesion detection apparatus 5 receives the three-dimensional MR image data from the medical image processing apparatus 7, and applies lesion detection processing to the received three-dimensional MR image data to detect the cerebrovascular lesion (step S2). The algorithm of the lesion detection processing relates to AI, threshold processing, and morphological operation, etc., and is not particularly limited. As the algorithm of AI, for example, a neural network, logistic regression, random forest, and support vector machine may be used. The cerebrovascular lesion to be detected by the lesion detection apparatus 5 is, specifically, an unruptured cerebral aneurysm, an intracranial artery stenosis, and a cerebrovascular dissection. One type or a plurality of types of lesions may be detected from among the unruptured cerebral aneurysm, the intracranial artery stenosis, and the cerebrovascular dissection. The coordinate information, the painting information, and the additional information are generated for each detection position of the cerebrovascular lesion. The coordinate information and the additional information are defined in accordance with the data format of the non-DICOM standard, such as a Java Script Object Notation (JSON) or an Extensible Markup Language (XML). The coordinate information and the additional information may be defined in accordance with the data format of the DICOM standard. The painting information is defined by a GSPS of the DICOM standard.

Figure 4:
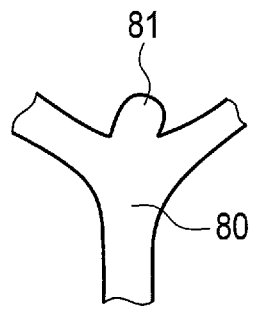
FIG. 4 is a schematic view showing an unruptured cerebral aneurysm.
Figure 5:
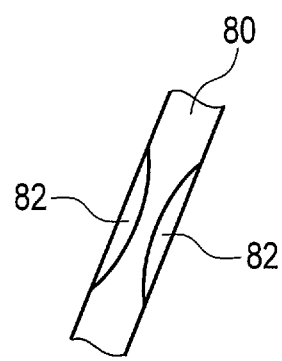
FIG. 5 is a schematic view showing an intracranial artery stenosis.
Figure 6:
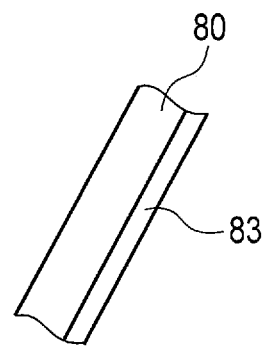
FIG. 6 is a schematic view showing a cerebrovascular dissection.

FIG. 4 is a schematic view of an unruptured cerebral aneurysm 81. As shown in FIG. 4, the unruptured cerebral aneurysm 81 is a bulging portion of a bifurcation, etc. of a cerebral blood vessel 80. The risk of rupture of the unruptured cerebral aneurysm 81 is evaluated by a rupture rate, etc. FIG. 5 is a schematic view of an intracranial artery stenosis. As shown in FIG. 5, the intracranial artery stenosis is a symptom in which a vascular wall of the cerebral blood vessel 80 becomes hypertrophic by arterial sclerosis 82, etc., and the intravascular lumen becomes narrow. The risk of stenosis of the intracranial artery stenosis is evaluated by a stenotic rate, etc. FIG. 6 is a schematic view of a cerebrovascular dissection. As shown in FIG. 6, the cerebrovascular dissection is a symptom in which the internal wall of the cerebral blood vessel 80 is dissociated, and blood flows into a dissociated portion 83. As the blood flows into the dissociated portion 83, an aneurysm is formed.

When the lesion detection processing is performed, the lesion detection apparatus 5 transmits the detection result, that is, the painting information, the coordinate information, and the additional information of each detection position, to the medical image processing apparatus 7. The communication interface 72 of the medical image processing apparatus 7 receives the detection result from the lesion detection apparatus 5. The received detection result acquiring the coordinate information of at least one detection position of the cerebrovascular lesion for the three-dimensional MR image data relating to the head part is stored in the storage circuitry 75.

The processing circuitry 71 of the medical image processing apparatus 7 displays a two-dimensional MR image (display image) based on the three-dimensional MR image data and the detection result relating to the cerebrovascular lesion (step S3). The display image and the detection result are shown on the display device 73 by realizing the display control function 714 of the processing circuitry 71. In the following, a cerebral aneurysm will be given as a specific example of the cerebrovascular lesion, and will be explained in detail in step S3.

In step S3, the processing circuitry 71 acquires the coordinate information of at least one detection position of the cerebrovascular lesion for the three-dimensional MR image data relating to the head part from the storage circuitry 75. Based on the three-dimensional MR image data and the coordinate information of at least one detection position, the processing circuitry 71 generates a two-dimensional display image which visualize a part of or all of the at least one detection position. As such a display image, a maximum value projection image that has a specific slab thickness is generated. For example, the specific slab thickness is a thickness in which the slab contains all of the detection positions selected by a user among all of the detected detection positions. Specifically, the processing circuitry 71 reads the coordinate information of all of the detection positions selected by the user, and calculates the position and the thickness of the slab containing all of such detection positions selected by the user. The processing circuitry 71 then sets the slab relating to the calculated position and thickness in the three-dimensional image data, performs maximum value projection processing exclusively on the set slab, and generates the maximum value projection image. In the generated maximum value projection image, cerebral aneurysm candidates of all of the detection positions selected by the user are painted. The processing circuitry 71 initially displays the generated maximum value projection image on the display device 73. When doing so, the processing circuitry 71 paints an annotation of a circular mark on the detection position in accordance with the painting information of all of the detection positions selected by the user. In this manner, by initially displaying the maximum value projection image with a specific slab thickness, the detection result of the cerebral aneurysm can be grasped more easily than in the case of the user confirming the slice images one by one.

Figure 7:
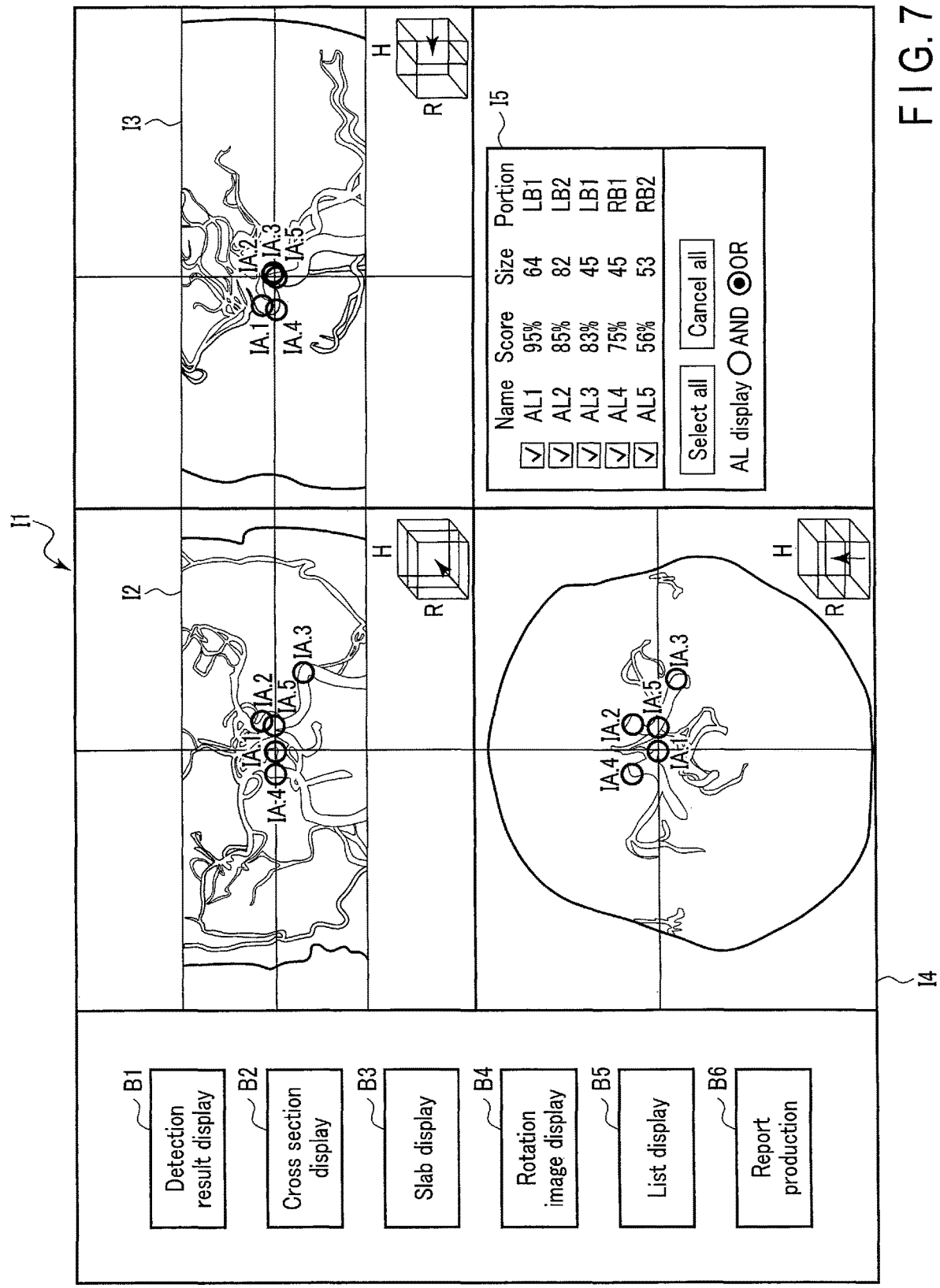
FIG. 7 shows an example of a display screen of a maximum value projection image and a detection result.

FIG. 7 shows an example of a display screen I1 of the maximum value projection image and the detection result. As shown in FIG. 7, as the maximum value projection image, a coronal cross-sectional maximum value projection image I2, a sagittal cross-sectional maximum value projection image I3, and an axial cross-sectional maximum value projection image I4 are displayed. A coronal cross section, a sagittal cross section, and an axial cross section are referred to as three orthogonal cross sections. The processing circuitry 71 calculates a specific slab thickness and slab position for each of the coronal cross section, the sagittal cross section, and the axial cross section. When the specific slab thickness and slab position for each of the coronal cross section, the sagittal cross section, and the axial cross section are calculated, the processing circuitry 71 sets a slab with the specific slab thickness and a slab position for each of the coronal cross section, the sagittal cross section, and the axial cross section in the three-dimensional MR image data. By applying the maximum value projection processing for each of the slabs, the processing circuitry 71 generates the coronal cross-sectional maximum value projection image I2, the sagittal cross-sectional maximum value projection image I3, and the axial cross-sectional maximum value projection image I4.

On the display screen I1, a detection result list I5 is displayed. The detection result list I5 is a list of additional information of each detection position relating to the cerebral aneurysm. The detection result list I5 is generated by the processing circuitry 71 based on the additional information of each detection position relating to the cerebral aneurysm. For example, as the additional information, a name, a score, a size, and a portion are displayed. The name displayed as "AL1", etc. is a name for identifying the detection position. The score displayed as "95%", etc. is an indicator that indicates the reliability at which the detection position includes the cerebral aneurysm, that is, the degree of certainty. The size displayed as "64", etc. indicates a volume of the detection position. The size may not only indicate a volume, but may also indicate a major axis or a minor axis, or may indicate a ratio between the major axis and the minor axis. The portion displayed as "LB1", etc. indicates a name of an anatomical location of a portion at which the detection position exists. In this manner, by displaying the additional information of each of the detection positions by character, the user is able to grasp the details of the additional information of each of the detection positions. Since the score, the size, and the portion are displayed, the user can determine the probability, etc. of the rupture of the cerebral aneurysm. It is clinically useful to display such additional information.

A selection box is displayed on a record of each detection position. Each detection position is selected by selecting a record corresponding to a desired detection position via the input interface 74. The selected detection positions are indicated by annotations in each of the maximum value projection images I2, I3, and I4. In FIG. 7, since the detection positions of "AL1" to "AL5" are selected, five annotations corresponding to five detection positions from "AL1" to "AL5" will be painted in each of the maximum value projection images I2, I3, and I4. Near each annotation, the name of the detection position indicated by the annotation is painted. In this manner, which of the plurality of detection positions displayed on the detection result list I5 the detection position indicated by the annotation is can be specified.

In the case where a part of the detection position displayed on the detection result list I5 is selected, the maximum value projection images I2, I3, and I4 are updated so that the detection position is limited to the selected part and displayed. Specifically, the thickness and the position of the slab are calculated to include the selected detection position in the slab, and the maximum value projection image relating to the slab in such a thickness and position is generated and displayed.

As shown in FIG. 7, on the display screen I1, a detection result display button B1, a cross section display button B2, a slab display button B3, a rotation image display button B4, a list display button B5, and a report producing button B6 are displayed. Buttons B1 to B6 are GUI buttons that can be selected via the input interface 74, etc. For example, by clicking on buttons B1 to B6 with a mouse, etc., buttons B1 to B6 can be switched between being selected or not selected.

In the case where the detection result display button B1 is selected, the processing circuitry 71 displays the coronal cross-sectional maximum value projection image I2, the sagittal cross-sectional maximum value projection image I3, and the axial cross-sectional maximum value projection image I4 which visualize all of the detection results. By selecting the detection result display button B1, even in the case where the cerebral aneurysm is detected at a plurality of positions, an oversight can be reduced.

In the case where the cross section display button B2 is selected, the mode transitions to a cross section display mode. In the cross section display mode, the processing circuitry 71 calculates the coronal cross section, the sagittal cross section, and the axial cross section including the detection position selected by the user based on the coordinate information of such detection position, and generates an MPR image relating to the calculated coronal cross section, an MPR image relating to the calculated sagittal cross section, and an MPR image relating to the calculated axial cross section by applying MPR processing to the three-dimensional MR image data. The MPR image relating to the coronal cross section, the MPR image relating to the sagittal cross section, and an MPR image relating to the axial cross section are displayed on the display screen I1. The processing circuitry 71 paints on each MPR image the annotation pointing out the detection position included in each MPR image.

In the above cross section display, only the annotation corresponding to the detection position included in each cross section will be painted in the MPR image. However, an annotation corresponding to a detection position positioned near each cross section may also be painted in the MPR image.

FIG. 8 is a schematic view showing the display of the annotation corresponding to a proximal detection position in the MPR image. As shown in FIG. 8, a plurality of detection positions P1 and P2 are assumed to be included in three-dimensional MR image data VO. A cross section SL1 set in the three-dimensional MR image data VO is assumed to be a display cross section. The display cross section SL1 has a thickness T1, which is the thickness of one voxel. An image component and an annotation included in the display cross section SL1 are painted in the MPR image by the MPR processing. In the three-dimensional MR image data VO, an annotation projection region SL2 is set adjacent to the cross section SL1. The annotation projection region SL2 has a thickness T2, which is thicker than one voxel. Although an image component included in the annotation projection region SL2 is not projected, an annotation corresponding to the detection position P1 included in the annotation projection region SL2 is projected. An annotation corresponding to a detection position P2 that is positioned in an image region farther from the display cross section SL1 than the annotation projection region SL2 is not projected.

The processing circuitry 71 generates an MPR image relating to the display cross section SL1 based on the three-dimensional MR image data VO, and projects the annotation corresponding to the detection position P1 included in the annotation projection region SL2 on the MPR image. The projection direction is set in a perpendicular direction of the display cross section SL1. In this manner, the MPR image relating to the display cross section SL1 in which the annotation corresponding to the detection position P1 positioned near the display cross section SL1 is painted is generated and displayed.

The thickness T2 can be set by any method. For example, the thickness T2 may be set to any value via the input interface 74, etc. Furthermore, the thickness T2 may also be automatically calculated to be a value that includes a detection position selected by a user.

In the case where the slab display button B3 is selected, the mode transitions to a slab display mode. In the slab display mode, the processing circuitry 71 calculates the coronal cross section, the sagittal cross section, and the axial cross section including the detection position selected by the user based on the coordinate information of such detection position, and generates a slab image relating to the calculated coronal cross section, a slab image relating to the calculated sagittal cross section, and a slab image relating to the calculated axial cross section based on the three-dimensional MR image data. A cross section that has a thickness of two or more voxels is also referred to as a slab.

In the above-described slab display, only the annotation corresponding to the detection position included in each slab will be painted in the slab image. However, an annotation corresponding to a detection position positioned near each slab may also be painted in the slab image.

FIG. 9 is a schematic view showing the display of the annotation corresponding to a proximal detection position in the slab image. As shown in FIG. 9, a plurality of detection positions P3, P4, and P5 are assumed to be included in three-dimensional MR image data VO. A slab SL3 set in the three-dimensional MR image data VO is assumed to be the slab to be displayed. The display slab SL3 has a thickness T3, which is a thickness of a plurality of voxels. An image component and an annotation corresponding to the detection position P3 included in the slab SL3 are painted in the slab image. In the three-dimensional MR image data VO, a region SL4 for painting the annotation (hereinafter referred to as an annotation projection region), which is adjacent to the display slab SL3, is set. The annotation projection region SL4 has a thickness T4, which is a thickness of a plurality of voxels. Although an image component included in the annotation projection region SL4 is not projected, an annotation corresponding to the detection position P4 included in the annotation projection region SL4 is projected. An annotation corresponding to a detection position P5 that is positioned in an image region farther from the slab SL3 than the annotation projection region SL4 is not projected.

The processing circuitry 71 generates a maximum value projection image relating to the display slab SL3 based on the three-dimensional MR image data VO, and projects the annotation corresponding to the detection position P4 included in the annotation projection region SL4 on the maximum value projection image. The projection direction is set in a perpendicular direction of the slab SL3. In this manner, the annotation corresponding to the detection position P4 positioned near the slab SL3 will be painted in the maximum value projection image relating to the slab SL3. The pixel value projection processing is not limited to the maximum value projection processing, and may be minimum value projection processing or average value projection processing, etc. according to a tissue or a substance that is being focused on.

The thicknesses T3 and T4 can be set by any method. For example, the thicknesses T3 and T4 may be set to any value via the input interface 74, etc. Furthermore, the thicknesses T3 and T4 may also be automatically calculated to be a value that includes a detection position selected by a user.

In the case where the rotation image display button B4 is selected, the mode transitions to a rotation display mode. In the rotation display mode, the processing circuitry 71 generates a rotation image relating to a vascular region included in the three-dimensional MR image data VO. The rotation image is a generic term of an MPR image, a slab image, and a volume rendering image, etc. generated per predetermined rotation angle about a predetermined rotation axis. By realizing the display control function 714, the rotation image is displayed on the display device 73. By displaying the rotation image, the detection result of the cerebral aneurysm can be easily grasped.

Figure 10:
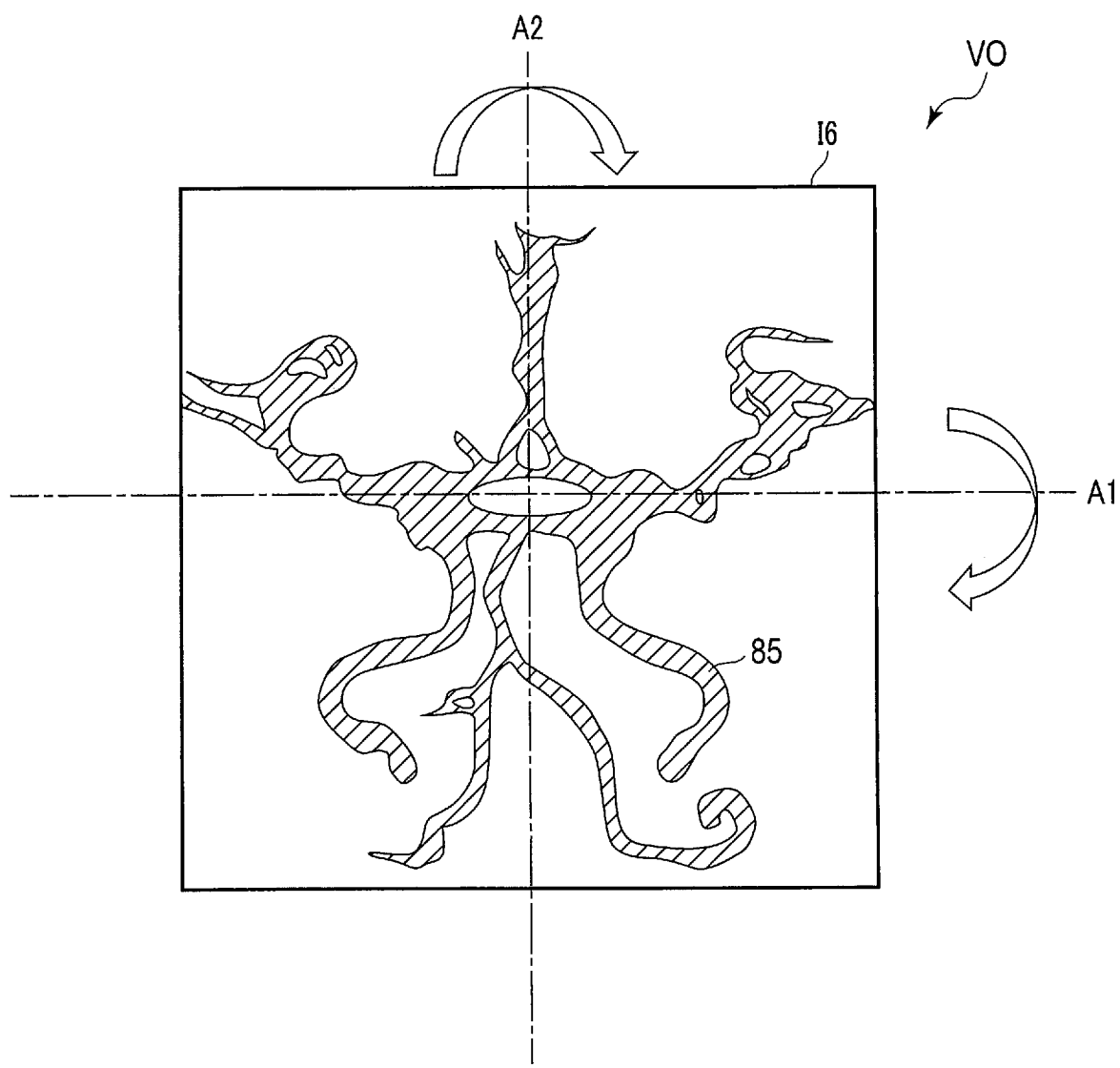
FIG. 10 is a schematic view showing a rotation image.

FIG. 10 is a schematic view showing a rotation image I6. As shown in FIG. 10, the three-dimensional MR image data includes a vascular region 85. First, by realizing the image generating function 712, the processing circuitry 71 extracts the vascular region included in the three-dimensional MR image data VO by performing image processing such as threshold processing. In order to perform extraction processing of the vascular region 85, an imaging method that is able to extract a blood vessel with a clear contrast is adopted. Then, by realizing the image generating function 712, the processing circuitry 71 generates an MPR image generated per predetermined rotation angle about a predetermined rotation axis based on the extracted vascular region.

For example, according to the "Guidelines for brain checkup" provided by the Japan Brain Dock Society, imaging by a 3D-TOF method is the principle method for detecting an unruptured cerebral aneurysm and blockage and stenotic lesion of the main artery of a head part. According to these guidelines, a maximum value projection method, etc. is used to produce (1) an image by horizontal rotation and (2) a reconstructed image by anteroposterior rotation centering around a circle of Willis.

Therefore, the processing circuitry 71 sets a rotation axis A1 relating to an anteroposterior direction and a rotation axis A2 relating to a horizontal direction to the three-dimensional MR image data VO or the vascular region 85. The processing circuitry 71 sets an MPR cross section for each predetermined angle about the rotation axis A1, and generates an MPR image for each MPR cross section as a rotation image. Alternatively, the processing circuitry 71 sets an MPR cross section for each predetermined angle about the rotation axis A2, and generates an MPR image for each MPR cross section as a rotation image. The predetermined rotation angle may be set to any value; however, for example, seven to ten degrees are preferable. The generated rotation image of the predetermined rotation angle is displayed on the display device 73. By a rotation operation performed by a user via the input interface 74, the rotation image displayed on the display device 73 is updated to a rotation image of a rotation angle in accordance with the rotation operation. According to the present embodiment, in this manner, the display image of the display method prescribed in the guidelines for brain checkup will be able to be almost automatically generated and displayed. Furthermore, since the processing necessary for generating an image conforming to the guidelines can be automatically performed based on the detection result, high-quality medical services can be widely provided to users and patients.

In the above-described processing, all of the vascular regions included in the three-dimensional MR image data are extracted; however, the present embodiment is not limited thereto. For example, only a vascular region including a detection position selected by the user in the detection result list I5 may be extracted, or only a vascular region selected by the user in a given display image of, for example, the slab image and the cross section image may be extracted. Furthermore, as the rotation axis, a rotation axis of any direction may be set without being limited to the rotation axis relating to the anteroposterior direction or the rotation axis relating to the horizontal direction.

In the case where the list display button B5 is selected, the processing circuitry 71 switches between display and non-display of the detection result list I5. In the manner described above, the processing circuitry 71 generates the detection result list I5 based on the additional information of each detection position relating to the cerebral aneurysm. For example, pressing an AL read button via the input interface 74, etc. may serve as a trigger for the processing circuitry 71 to read the detection result relating to target three-dimensional MR image data of a target patient, and generate the detection result list I5 based on the additional information of each detection position relating to the detection result. The detection result list I5 is displayed in a predetermined display frame of the display screen I1. In the case where the detection result list I5 is switched to a non-display, a cross section image (an oblique image), etc. relating to any cross section may be displayed.

In the manner described above, each detection position displayed on the detection result list I5 can be selected via the input interface 74, etc. In the case where the detection position is selected in the cross section display mode, an MPR image relating to the selected detection position is displayed, and an annotation pointing out the detection position is painted on the MPR image. In the case where the detection position is selected in the slab display mode, a slab image relating to the selected detection position is displayed, and an annotation pointing out the detection position is painted on the slab image. In other words, the display cross section or the display slab moves to the cross section or slab including the selected detection position, and the annotation is exclusively painted on the selected detection position. In this manner, the viewability of the detection position selected by the user can be improved.

In the case where the report producing button B6 is selected, by realizing the report producing function 713, the processing circuitry 71 produces a report relating to the detection result of the cerebral aneurysm (hereinafter referred to as a cerebral aneurysm report).

Figure 11:
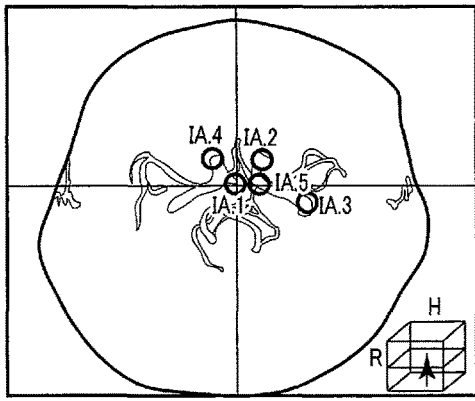
FIG. 11 shows an example of a cerebral aneurysm report.

FIG. 11 shows an example of a cerebral aneurysm report R1. As shown in FIG. 11, the cerebral aneurysm report R1 is electronic data including information relating to a site and size of each detection position of the cerebral aneurysm. For example, the cerebral aneurysm report R1 is produced for a detection position that is determined to be an aneurysm as a result of the user interpreting a radiogram, etc. The cerebral aneurysm report R1 specifically includes patient information R2, detection result information R3, and a key image I7.

The patient information R2 includes basic information regarding the full name, age, and gender, etc. of a patient. The patient information R2 can, for example, be extracted from the attendant information of the three-dimensional MR image data. The detection result information R3 is a list of additional information of each detection position. The additional information includes the name, score, size, portion, rupture rate, and a treatment method R4. The name is a name for identifying the detection portion. The score is an indicator that indicates the degree of reliability in which the detection position is a cerebral aneurysm. The size indicates a volume of the detection position. The size may not only indicate the volume, but also may indicate a major axis or a minor axis, or may be a ratio between the major axis and the minor axis. The portion indicates aflame of an anatomical location of a portion in which the detection position exists. The rupture rate is an indicator that indicates the risk of rupture of the cerebral aneurysm of the detection position. By realizing the report producing function 713, the processing circuitry 71 calculates the rupture rate based on the patient information R2 and the detection result information R3. Specifically, the rupture rate is calculated in accordance with a predetermined algorithm or a look-up table (LUT) based on the race, the age, and the gender in the patient information R2 and the size and the portion in the detection result information R3. The treatment method R4 indicates the degree of recommendation of a standard treatment method with respect to the cerebral aneurysm at the detection position. The treatment method R4 includes progress observation, surgical clipping, and coil embolization. By realizing the report producing function 713, the processing circuitry 71 calculates the degree of recommendation of the treatment method R4 based on the patient information R2 and the detection result information R3. Specifically, the degree of recommendation of the treatment method R4 is calculated in accordance with a predetermined algorithm or an LUT based on the race, the age, and the gender in the patient information R2 and the size and the portion in the detection result information R3. For example, the detection position of the name "AL2" will have a score of "85%", a size of "82", a portion "LB2", a rupture rate of "80%", a progress observation of "20%", a surgical clipping of "80%", and a coil embolization of "80%".

The key image I7 is a reduced image of the display screen in which the detection result is clearly visualized. For example, as the key image I7, the processing circuitry 71 generates a reduced image of the slab image relating to the axial cross section, in which all of the detection positions "AL1" to "AL5" are visualized. It is preferable to have annotations pointing out each detection position visualized in the key image I7. The generated key image I7 is attached to the cerebral aneurysm report R1. There is no need to have all of the detection positions "AL1" to "AL5" visualized in the key image I7. For example, a key image may be generated for each of the detection positions. The key image I7 does not have to be a slab image, and may be an MPR image, a rotation image, etc., or any display image. Furthermore, instead of the key image I7, a display image prior to the reduction may also be attached.

The generated cerebral aneurysm report R1 is displayed on the display device 73. The displayed cerebral aneurysm report R1 is observed by a user such as a radiologist. The cerebral aneurysm report R1 may also be transferred to other computers such as a viewer via the network, and displayed on the display device of such computer. According to the present embodiment, since the cerebral aneurysm report R1 is automatically produced based on the detection result information R3, the trouble of producing the cerebral aneurysm report R1 may be reduced for the user.

The cerebral aneurysm report R1 does not need to include all of the items described above. For example, the rupture rate and the treatment method, etc. do not necessarily have to be included. Furthermore, the coordinate information of each detection position may be displayed as the detection result information R3. The user's observation or memo, etc. may also be attached to the cerebral aneurysm report R1.

The medical image processing system 1 according to the present embodiment is used for, for example, regular physical checkups relating to the head part of a subject. That is, a certain patient may have the detection result of the cerebral aneurysm periodically acquired by the lesion detection apparatus 5. Therefore, time-series information relating to the detection result may be attached to the cerebral aneurysm report. As the time-series information relating to the detection result, for example, a report (hereinafter referred to as a lump size report) relating to a graph (hereinafter referred to as a lump size graph) in which the size of the detection position (hereinafter referred to as a lump size) changes in time-series is generated.

FIG. 12 shows an example of a lump size report R5. As shown in FIG. 12, the time-series information of the lump size relating to each detection position is described in the lump size report R5. Specifically, a graph R6 and a list R7 relating to the lump size are included in the lump size report R5. The graph R6 is a line graph in which an acquisition date of the three-dimensional MR image data is defined in a horizontal axis, and the lump size [mm] is defined in a vertical axis. The list R7 describes a lump size of each detection position for each acquisition date by a numeric value.

The lump size is stored in the storage circuitry 75 in association with at least the name of the detection position and the acquisition date. In the case where an instruction to produce the lump size report R5 is issued, by realizing the report producing function 713, the processing circuitry 71 reads information relating to a lump size for each detection position from the storage circuitry 75. The processing circuitry 71 produces the graph R6 and the list R7 based on the lump size for each detection position, and attaches them to the lump size report R5. The lump size report R5 may be incorporated into the cerebral aneurysm report R1, or may be produced as an independent report. The detection position for which the lump size report R5 is to be produced may be limited to that determined to be an aneurysm by the user's interpretation of the radiogram, etc.

The generated lump size report R5 is displayed on the display device 73, and is observed by the user. In this manner, the user will be able to easily grasp the time-series information of the lump size. Furthermore, the lump size report R5 can be automatically produced based on the information relating to the lump size for each acquisition date. This will allow the user to reduce the trouble of producing the lump size report R5. The lump size report R5 may also be transferred to other computers such as a viewer via the network, and displayed on the display device of such a computer.

The time-series information relating to the detection result is not limited to only the time-series information of the lump size. For example, the time-series information of the degree of recommendation of the score, the rupture rate, and the treatment method may be generated according to the purpose.

As other time-series information relating to the detection result, an image temporal difference may also be generated.

FIG. 13 is a schematic view showing a generation process of the image temporal difference. An MPR image relating to each detection position is stored in the storage circuitry 75 in association with an acquisition date and the name of the detection position, etc. For example, an MPR image I8 of an acquisition date "2018/1/1" and an MPR image I9 of the next acquisition date "2018/4/1" are stored in the storage circuitry 75. The MPR image I8 includes a detection position 86, and the MPR image I9 includes a detection position 87. The detection position 86 included in the MPR image I8 and the detection position 87 included in the MPR image I9 are anatomically the same detection position.

In the case where a display instruction of the image temporal difference is issued, the processing circuitry 71 reads the MPR image I8 of the acquisition date "2018/1/1" and the MPR image I9 of the next acquisition date "2018/4/1" relating to the same cerebral aneurysm from the storage circuitry 75, and generates a differential image 110 of the MPR image I8 and the MPR image I9. The differential image 110 includes a differential region 88 of the detection position 86 included in the MPR image I8 and the detection position 87 included in the MPR image I9. The differential image 110 is attached to the aneurysm report R1 or displayed on the display device 73. By observing the size, etc. of the differential region 88, the user grasps the change in the form of the cerebral aneurysm with time. The processing circuitry 71 may compare the size of the differential region 88 with a given threshold, and, in the case where the size of the differential region 88 is larger than the threshold, may attach an alert to the aneurysm report R1. In this manner, it is possible to give notice that the aneurysm requires attention.

Instead of generating a differential image of two temporally adjacent MPR images, the processing circuitry 71 may generate a differential image of two MPR images obtained at given acquisition dates. Furthermore, in the case where the MPR images are stored in the storage circuitry 75 over three or more acquisition dates, the processing circuitry 71 may generate differential images sequentially for the MPR images with adjacent acquisition dates. In this manner, the time-series differential image is generated. At this time, it is preferable to display the differential images in parallel with each other on the display device 73, or to attach them to the aneurysm report. Furthermore, the differential images may also be those of the slab images instead of those of the MPR images. In this case, each slab image may include a plurality of detection positions instead of one detection position.

In the above explanation, as an example, the cerebrovascular lesion was assumed to be a type of unruptured cerebral aneurysm. However, the lesion detection apparatus 5 may detect at least two types among the unruptured cerebral aneurysm, the intracranial artery stenosis, and the cerebrovascular dissection. In this case, the lesion detection apparatus 5 outputs character information (hereinafter referred to as lesion type information) indicating the type of lesion further in addition to the name and size, etc. for each detection position as additional information. In the same manner as the above-described processing, the processing circuitry 71 generates a display image in which the detection position can be easily grasped.

FIG. 14 shows a display example of the detection positions of the unruptured cerebral aneurysm, the intracranial artery stenosis, and the cerebrovascular dissection. As shown in FIG. 14, in the same manner as the above-described processing, the processing circuitry 71 generates a maximum value projection image I11 relating to a slab including detection positions of the unruptured cerebral aneurysm, the intracranial artery stenosis, and the cerebrovascular dissection, and simultaneously displays annotations pointing out each detection position on the maximum value projection image I11. When doing so, the processing circuitry 71 paints annotations in forms that differ in accordance with the type of lesion on the maximum value projection image I11. By referring to the LUT in which the lesion type information and the annotation form are associated, the processing circuitry 71 determines the annotation form to be used for each detection position. For example, as shown is FIG. 14, a solid line annotation is used for the detection position of the unruptured cerebral aneurysm, a dotted line annotation is used for the detection position of the intracranial artery stenosis, and a double line annotation is used for the detection position of the cerebrovascular dissection. By painting such annotations in forms that differ in accordance with the type of lesion, the user can easily notice the lesion indicated by the annotation only by observing the form of the annotation.

Furthermore, the annotation in the above-described processing is a circular mark that points out the detection position of each lesion of the unruptured cerebral aneurysm, the intracranial artery stenosis, and the cerebrovascular dissection. However, as the annotation, a mark that has different forms in accordance with the type of lesion may also be painted. For example, the marks of the annotation may preferably be circular for the annotation relating to the unruptured cerebral aneurysm, triangular for the annotation relating to the intracranial artery stenosis, and quadrangular for the annotation relating to the cerebrovascular dissection. By using annotations in shapes that differ in accordance with the type of lesion in this manner, the user can easily specify the type of lesion indicated by the annotation by recognizing the shape of the annotation.

Furthermore, in the above-described processing, the annotation is painted at the detection position. However, the present embodiment is not limited thereto. For example, the image region corresponding to each lesion included in the display image may be highlighted.

FIG. 15 shows a highlighted example of the unruptured cerebral aneurysm. As shown in FIG. 15, an image region corresponding to the unruptured cerebral aneurysm is a bulging portion 91 of a bifurcation, etc. of the cerebral blood vessel 80. The processing circuitry 71 highlights the bulging portion 91 by filling in the portion with a given color. FIG. 16 shows a highlighted example of the intracranial artery stenosis. As shown in FIG. 16, an image region corresponding to the intracranial artery stenosis is a hypertrophic portion 92 of a vascular wall of the cerebral blood vessel 80 caused by arterial sclerosis, etc. The processing circuitry 71 highlights the hypertrophic portion 92 by filling in the portion with a given color. FIG. 17 shows a highlighted example of the cerebrovascular dissection. As shown in FIG. 17, an image region corresponding to the cerebrovascular dissection is a dissociated portion 93 of an internal wall of the cerebral blood vessel 80. The processing circuitry 71 highlights the dissociated portion 93 by filling in the portion with a given color. In this manner, by filling in the image region corresponding to each lesion with a given color, the user will be able to grasp the form and the existing range, etc. of the lesion region.

The given colors of each lesion may be set to be colors that are different from each other. For example, preferably, the image region corresponding to the unruptured cerebral aneurysm may be filled in with green, the image region corresponding to the intracranial artery stenosis may be filled in with yellow, and the image region corresponding to the cerebrovascular dissection may be filled in with red. By filling in the image region corresponding to each lesion with given colors that are different from each other, the lesion type can be determined easily.

As explained above, the medical image processing apparatus 7 according to the present embodiment implements the processing circuitry 71. By executing the information acquisition function 711, the processing circuitry 71 acquires coordinate information of at least one detection position of the cerebrovascular lesion for the three-dimensional MR image data relating to the head part. By executing the image generating function 712, the processing circuitry 71 generates a two-dimensional display image which visualize a part of or all of at least one detection position based on the three-dimensional MR image data and the coordinate information.

According to at least one of the embodiments explained above, it is possible to generate an image in which the detection position of the cerebrovascular lesion can be easily grasped.

The term "processor" used in the above explanation indicates, for example, a circuit, such as a CPU, a GPU, or an application specific integrated circuit (ASIC), and a programmable logic device (for example, a simple programmable logic device (SPLD), a complex programmable logic device (CPLD), and a field programmable gate array (FPGA)). The processor reads and executes programs stored in the storage circuitry to realize respective functions thereof. Instead of storing the programs in the storage circuitry, the programs may be incorporated directly into circuitry of the processor. In this case, the processor reads and executes the programs incorporated into the circuitry to realize the respective functions. Furthermore, instead of executing the programs, functions corresponding to the programs may also be executed by a combination of logic circuits. Each processor of the present embodiment is not limited to the case of being configured as a single circuit for each processor. Therefore, one processor may be configured by a combination of a plurality of independent circuits, and execute the functions thereof. Furthermore, a plurality of constituent elements in FIG. 1 and FIG. 2 may be integrated into one processor, and may realize the respective functions thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising processing circuitry configured to:
   acquire coordinate information of at least one detection position of a cerebrovascular lesion for three-dimensional MR image data relating to a head part; and
   generate a two-dimensional display image which visualize a part of or all of the at least one detection position based on the three-dimensional MR image data and the coordinate information.

2. The medical image processing apparatus according to claim 1, wherein the processing circuitry is configured to:
   calculate a slab thickness including a part of or all of the at least one detection position, and
   generate, as the two-dimensional display image, a slab image having the slab thickness based on the three-dimensional MR image data.

3. The medical image processing apparatus according to claim 2, wherein the processing circuitry is configured to:
   calculate a slab thickness including a part of or all of the at least one detection position relating to three orthogonal cross sections, and
   generate a slab image of the three orthogonal cross sections with the slab thickness.

4. The medical image processing apparatus according to claim 2, wherein the processing circuitry is configured to generate, as the slab image, a maximum value projection image based on the three-dimensional MR image data.

5. The medical image processing apparatus according to claim 1, wherein the processing circuitry is configured to:
  extract a vascular region including the at least one detection position from the three-dimensional MR image data, and
  generate, as the two-dimensional display image, a rotation image for each predetermined direction and predetermined angle relating to the vascular region.

6. The medical image processing apparatus according to claim 5, wherein the predetermined direction is a horizontal direction and an anteroposterior direction centering around a circle of Willis.

7. The medical image processing apparatus according to claim 1, further comprising a display device displaying the two-dimensional display image.

8. The medical image processing apparatus according to claim 7, wherein the display device superimposes a mark on the at least one detection position included in the two-dimensional display image.

9. The medical image processing apparatus according to claim 1, further comprising:
  a display device, wherein
  the processing circuitry is configured to
  calculate a first slab thickness for the display, and a second slab thickness, which is thicker than the first slab thickness, for painting a mark, and
  generate, as the two-dimensional display image, a slab image having the first slab thickness based on the three-dimensional MR image data, and
  the display device adds a mark to the at least one detection position included in the second slab thickness in the slab image.

10. The medical image processing apparatus according to claim 1, further comprising:
  a display device, wherein
  the processing circuitry is configured to further acquire at least one piece of character information from among a name, a site, a score, and a size of the at least one detection position, and
  the display device displays a list of the character information of the at least one detection position.

11. The medical image processing apparatus according to claim 10, wherein the display device paints a mark exclusively to a detection position designated by a user in the at least one detection position included in the list.

12. The medical image processing apparatus according to claim 1, wherein the cerebrovascular lesion is one of a cerebral aneurysm, a stenosis, or a vascular dissection.

13. The medical image processing apparatus according to claim 1, wherein the processing circuitry is configured to:
  further acquire at least one piece of character information from among a name, a site, a score, and a size of a detected lesion of the at least one detection position, and
  produce a report regarding the at least one detection position based on the character information of the at least one detection position.

14. The medical image processing apparatus according to claim 13, wherein the processing circuitry attaches the two-dimensional display image or a reduced image of the two-dimensional display image to the report.

15. The medical image processing apparatus according to claim 13, wherein
  the cerebrovascular lesion is a cerebral aneurysm, and
  the processing circuitry attaches a graph showing a time-series change of a size relating to the at least one detection position to the report.

16. The medical image processing apparatus according to claim 13, wherein
  the cerebrovascular lesion is a cerebral aneurysm, and
  the processing circuitry attaches a rupture rate relating to the at least one detection position to the report.

17. The medical image processing apparatus according to claim 13, wherein the processing circuitry attaches a treatment method relating to the at least one detection position to the report.

18. The medical image processing apparatus according to claim 1, further comprising a display device displaying a subtraction image of the two-dimensional display image and a two-dimensional display image of another date and time relating to a same subject.

19. The medical image processing apparatus according to claim 1, further comprising a communication device to transmit the three-dimensional MR image data to a lesion detection apparatus in order to detect a cerebrovascular lesion included in the three-dimensional MR image data by image processing, and acquire coordinate information of the at least one detection position by the processing circuitry.

20. A medical image processing system comprising:
  a detection apparatus detecting at least one lesion region relating to a cerebrovascular lesion included in three-dimensional MR image data relating to a head part, and specifying coordinate information of a detection position of the at least one detected lesion region;
  a generation apparatus generating a two-dimensional display image which visualize a part of or all of the at least one detection position based on the three-dimensional MR image data and the coordinate information; and
  a display apparatus displaying the two-dimensional display image.

* * * * *